(12) United States Patent
Zanella (10) Patent No.: US 7,584,003 B2
(45) Date of Patent: Sep. 1, 2009

(54) APPARATUS OF ELECTRO-STIMULATION AND RELATIVE DATA SUPPORT

(75) Inventor: Andrea Zanella, Mirandola (IT)

(73) Assignee: Lorenz Biotech S.p.A., Medolla (IT)

( * ) Notice: Subject to any disclaimer, the term of this patent is extended or adjusted under 35 U.S.C. 154(b) by 462 days.

(21) Appl. No.: 10/541,592

(22) PCT Filed: Jan. 28, 2004

(86) PCT No.: PCT/EP2004/000724

§ 371 (c)(1),
(2), (4) Date: Jul. 7, 2005

(87) PCT Pub. No.: WO2004/067087

PCT Pub. Date: Aug. 12, 2004

(65) Prior Publication Data
US 2006/0052845 A1    Mar. 9, 2006

(30) Foreign Application Priority Data
Jan. 28, 2003  (IT) .......................... MO2003A0019

(51) Int. Cl.
*A61N 1/00* (2006.01)
(52) U.S. Cl. .......................................... 607/66; 607/72
(58) Field of Classification Search ................... 607/66, 607/72
See application file for complete search history.

(56) References Cited

U.S. PATENT DOCUMENTS

| | | | |
|---|---|---|---|
| 4,240,437 A | 12/1980 | Church | |
| 4,977,895 A | 12/1990 | Tannenbaum | |
| 6,029,090 A * | 2/2000 | Herbst | 607/66 |
| 2002/0055762 A1 | 5/2002 | Gliner | |
| 2002/0165591 A1 | 11/2002 | Piccone | |

FOREIGN PATENT DOCUMENTS

| | | |
|---|---|---|
| IT | MI2000A 001733 | 1/2002 |
| WO | 99/37359 | 7/1999 |

OTHER PUBLICATIONS

International Search Report of PCT/EP2004/000724, dated Jun. 14, 2004.
US 4,451,432 A, 09/1985, Garceau et al. (withdrawn).
Declaration of Mr.DeVincolis concerning alleged prior sales in Italy, with two invoices and computer printouts.
CD-ROM containing software referred to in Declaration of Mr. DeVincolis.

(Continued)

*Primary Examiner*—Scott M Getzow
(74) *Attorney, Agent, or Firm*—Nixon & Vanderhye, PC (57) ABSTRACT

Example electro-stimulation apparatuses and methods involve generating pulses having preset values of typical parameters. A number of sub-phases forming a sequence of the pulses are applied to organism, the sequence including an initial pulse an a final pulse. A substantial variation of at least one typical parameter is performed at a moment between the initial pulse and the final pulse. The frequency of the pulses is varied by causing between two consecutive sub-phases a frequency discontinuity greater than 60 Hz preceded by sub-phases having non-constant frequencies.

57 Claims, 7 Drawing Sheets

OTHER PUBLICATIONS

Brochure enclosed with Declaration of Mr. DeVincolis.
English translation of Declaration of Mr.DeVincolis.
Declaration of Ms. Supino concerning alleged prior sales in Italy with computer printouts.
English translation of Declaration of Ms. Supino.
Declaration of Mr. Fanton concerning alleged prior sales in Italy, with computer printouts and invoices.
Statement: English translation of Declaration of Mr. Fanton concerning alleged prior sales in Italy.
Notice of Opposition to a European Patent, Oct. 8, 2008.
Response to Notice of Opposition, Mar. 27, 2009.

* cited by examiner

| SUB-PHASE | SUB-PHASE DURATION [s] | FREQUENCY [Hz] | PULSE WIDTH [μs] | BIOREACTION [μs] |
|---|---|---|---|---|
| 1 | 20 | 1 | 10 | 999990 |
| 2 | 5 | 1 | 20 | 999980 |
| 3 | 3 | 1 | 40 | 999960 |
| 4 | 1 | 2 | 40 | 499960 |
| 5 | 1 | 3 | 40 | 333293 |
| 6 | 1 | 4 | 40 | 249960 |
| 7 | 1 | 5 | 40 | 199960 |
| 8 | 1 | 6 | 40 | 166627 |
| 9 | 1 | 7 | 40 | 142817 |
| 10 | 1 | 8 | 40 | 124960 |
| 11 | 1 | 9 | 40 | 111071 |
| 12 | 1 | 19 | 40 | 52592 |
| 13 | 1 | 29 | 40 | 34443 |
| 14 | 4 | 1 | 10 | 999990 |
| 15 | 2 | 1 | 20 | 999980 |
| 16 | 2 | 1 | 40 | 999960 |
| 17 | 1 | 2 | 40 | 499960 |
| 18 | 2 | 3 | 40 | 333293 |
| 19 | 1 | 4 | 40 | 249960 |
| 20 | 2 | 5 | 40 | 199960 |
| 21 | 1 | 6 | 40 | 166627 |
| 22 | 2 | 7 | 40 | 142817 |
| 23 | 1 | 8 | 40 | 124960 |
| 24 | 2 | 9 | 40 | 111071 |
| 25 | 1 | 19 | 40 | 52592 |
| 26 | 1 | 29 | 40 | 34443 |
| 27 | 1 | 39 | 40 | 25601 |

Fig. 1

| SUB-PHASE | SUB-PHASE DURATION [s] | FREQUENCY [Hz] | PULSE WIDTH [µs] | BIOREACTION [µs] |
|---|---|---|---|---|
| 1 | 20 | 1 | 10 | 999990 |
| 2 | 3 | 1 | 20 | 999980 |
| 3 | 3 | 1 | 40 | 999960 |
| 4 | 1 | 2 | 40 | 499960 |
| 5 | 1 | 3 | 40 | 333293 |
| 6 | 1 | 4 | 40 | 249960 |
| 7 | 1 | 5 | 40 | 199960 |
| 8 | 4 | 6 | 20 | 166647 |
| 9 | 4 | 6 | 40 | 166627 |
| 10 | 4 | 6 | 20 | 166647 |
| 11 | 4 | 6 | 40 | 166627 |
| 12 | 4 | 7 | 20 | 142837 |
| 13 | 4 | 7 | 40 | 142817 |
| 14 | 4 | 7 | 20 | 142837 |
| 15 | 4 | 7 | 40 | 142817 |
| 16 | 1 | 8 | 40 | 124960 |
| 17 | 1 | 9 | 40 | 111071 |
| 18 | 1 | 19 | 40 | 52592 |
| 19 | 1 | 29 | 40 | 34443 |

Fig. 2

| | | | Sequences of muscular relaxation | | Sequences of microcirculatory system activation | | | | Freq. 100 Hz – Width 40 µs | | |
|---|---|---|---|---|---|---|---|---|---|---|---|
| Time [minutes] | -10 | -5 | 0 | 1 | 2 | 3 | 4 | 5 | 7 | 10 | 20 | 40 |
| VEGF values [pg/ml] in healthy subjects | 25,0 | 21,0 | 23,0 | 32,0 | 61,0 | 63,0 | 82,0 | 82,0 | 101,0 | 103,0 | | |
| VEGF values [pg/ml] in patients affected by vascular pathology | 17,7 | 31,0 | 31,1 | 19,7 | 22,3 | 19,0 | 27,3 | 34,3 | 44,7 | 42,3 | 33,2 | 40,2 |
| VEGF values [pg/ml] in diabetic patients affected by vascular pathology | 20,0 | 34,0 | 35,0 | 19,0 | 21,0 | 44,0 | 50,0 | 58,2 | 60,0 | 61,0 | 39,1 | 42,0 |

Fig. 5

| SUB-PHASE | SUB-PHASE DURATION [s] | FREQUENCY [Hz] | PULSE WIDTH [µs] | BIOREACTION [µs] |
|---|---|---|---|---|
| 1 | 20 | 1 | 10 | 999990 |
| 2 | 5 | 1 | 20 | 999980 |
| 3 | 3 | 1 | 40 | 999960 |
| 4 | 1 | 2 | 40 | 499960 |
| 5 | 1 | 3 | 40 | 333293 |
| 6 | 1 | 4 | 40 | 249960 |
| 7 | 1 | 5 | 40 | 199960 |
| 8 | 1 | 6 | 40 | 166627 |
| 9 | 1 | 7 | 40 | 142817 |
| 10 | 1 | 8 | 40 | 124960 |
| 11 | 1 | 9 | 40 | 111071 |
| 12 | 1 | 19 | 40 | 52592 |
| 13 | 8 | 1 | 10 | 999990 |
| 14 | 4 | 1 | 20 | 999980 |
| 15 | 2 | 1 | 30 | 999970 |
| 16 | 1 | 1 | 40 | 999960 |
| 17 | 8 | 2 | 40 | 499960 |
| 18 | 4 | 3 | 40 | 333293 |
| 19 | 2 | 4 | 40 | 249960 |
| 20 | 1 | 5 | 40 | 199960 |
| 21 | 8 | 6 | 10 | 166657 |
| 22 | 4 | 6 | 20 | 166647 |
| 23 | 2 | 6 | 30 | 166637 |
| 24 | 1 | 6 | 40 | 166627 |
| 25 | 8 | 7 | 40 | 142817 |
| 26 | 4 | 8 | 40 | 124960 |
| 27 | 2 | 9 | 40 | 111071 |
| 28 | 1 | 10 | 40 | 99960 |
| 29 | 4 | 11 | 20 | 90889 |
| 30 | 4 | 11 | 40 | 90869 |
| 31 | 4 | 11 | 20 | 90889 |
| 32 | 4 | 11 | 40 | 90869 |
| 33 | 4 | 11 | 20 | 90889 |
| 34 | 4 | 11 | 40 | 90869 |
| 35 | 4 | 11 | 20 | 90889 |
| 36 | 4 | 11 | 40 | 90869 |
| 37 | 4 | 11 | 20 | 90889 |
| 38 | 4 | 11 | 40 | 90869 |
| 39 | 1 | 21 | 40 | 47579 |
| 40 | 1 | 31 | 40 | 32218 |
| 41 | 1 | 41 | 40 | 24350 |

| SUB-PHASE | SUB-PHASE DURATION [s] | FREQUENCY [Hz] | PULSE WIDTH [µs] | BIOREACTION [µs] |
|---|---|---|---|---|
| 1 | 30 | 1 | 1 | 999990 |
| 2 | 5 | 1 | 2 | 999980 |
| 3 | 5 | 1 | 4 | 999960 |
| 4 | 1 | 2 | 4 | 499960 |
| 5 | 1 | 3 | 4 | 333293 |
| 6 | 1 | 4 | 4 | 249960 |
| 7 | 1 | 5 | 4 | 199960 |
| 8 | 1 | 6 | 4 | 166627 |
| 9 | 1 | 7 | 4 | 142817 |
| 10 | 1 | 8 | 4 | 124960 |
| 11 | 1 | 9 | 4 | 111071 |
| 12 | 30 | 11 | 2 | 90889 |
| 13 | 4 | 11 | 4 | 90869 |
| 14 | 30 | 11 | 2 | 90889 |
| 15 | 4 | 15 | 4 | 66627 |
| 16 | 2 | 16 | 4 | 62460 |
| 17 | 2 | 19 | 4 | 52592 |
| 18 | 30 | 1 | 1 | 999990 |
| 19 | 5 | 1 | 2 | 999980 |
| 20 | 5 | 1 | 4 | 999960 |
| 21 | 1 | 2 | 4 | 499960 |
| 22 | 1 | 3 | 4 | 333293 |
| 23 | 1 | 4 | 4 | 249960 |
| 24 | 1 | 5 | 4 | 199960 |
| 25 | 1 | 6 | 4 | 166627 |
| 26 | 1 | 7 | 4 | 142817 |
| 27 | 1 | 8 | 4 | 124960 |
| 28 | 1 | 9 | 4 | 111071 |
| 29 | 1 | 19 | 4 | 52592 |
| 39 | 8 | 1 | 1 | 999990 |
| 30 | 4 | 1 | 2 | 999980 |
| 31 | 2 | 1 | 3 | 999970 |
| 32 | 1 | 1 | 4 | 999960 |
| 33 | 8 | 2 | 4 | 499960 |
| 34 | 4 | 3 | 4 | 333293 |
| 35 | 2 | 4 | 4 | 249960 |
| 36 | 1 | 5 | 4 | 199960 |
| 37 | 8 | 6 | 1 | 166657 |
| 38 | 4 | 6 | 2 | 166647 |
| 39 | 2 | 6 | 3 | 166637 |

Fig. 8

| SUB-PHASE | SUB-PHASE DURATION [s] | FREQUENCY [Hz] | PULSE WIDTH [µs] | BIOREACTION [µs] |
|---|---|---|---|---|
| 40 | 1 | 6 | 4 | 166627 |
| 41 | 8 | 7 | 4 | 142817 |
| 42 | 4 | 8 | 4 | 124960 |
| 43 | 2 | 9 | 4 | 111071 |
| 44 | 1 | 10 | 4 | 99960 |
| 45 | 4 | 11 | 2 | 90889 |
| 46 | 4 | 11 | 4 | 90869 |
| 47 | 4 | 11 | 2 | 90889 |
| 48 | 4 | 11 | 4 | 90869 |
| 49 | 4 | 11 | 2 | 90889 |
| 50 | 4 | 11 | 4 | 90869 |
| 51 | 4 | 11 | 2 | 90889 |
| 52 | 4 | 11 | 4 | 90869 |
| 53 | 4 | 11 | 2 | 90889 |
| 54 | 4 | 11 | 4 | 90869 |
| 55 | 1 | 21 | 4 | 47579 |
| 56 | 1 | 31 | 4 | 32218 |
| 57 | 1 | 41 | 4 | 24350 |
| 58 | 60 | 2 | 1 | 499990 |
| 59 | 30 | 2 | 2 | 499980 |
| 60 | 15 | 2 | 4 | 499960 |
| 61 | 30 | 4 | 4 | 249960 |
| 62 | 1 | 8 | 2 | 124980 |
| 63 | 1 | 16 | 1 | 62490 |
| 64 | 1 | 8 | 2 | 124980 |
| 65 | 1 | 4 | 4 | 249960 |
| 66 | 30 | 6 | 4 | 166627 |
| 67 | 2 | 12 | 2 | 83313 |
| 68 | 2 | 24 | 2 | 41647 |
| 69 | 2 | 24 | 2 | 41647 |
| 70 | 2 | 24 | 3 | 41637 |
| 71 | 2 | 24 | 4 | 41627 |
| 72 | 30 | 30 | 4 | 33293 |
| 73 | 20 | 40 | 4 | 24960 |
| 74 | 60 | 50 | 4 | 19960 |
| 75 | 30 | 60 | 4 | 16627 |
| 76 | 60 | 90 | 4 | 11071 |
| 77 | 60 | 130 | 4 | 7652 |
| 78 | 40 | 160 | 4 | 6210 |
| 79 | 1 | 200 | 4 | 4960 |
| 80 | 120 | 220 | 4 | 4505 |

Fig. 9

APPARATUS OF ELECTRO-STIMULATION AND RELATIVE DATA SUPPORT

This application is the US national phase of international application PCT/EP2004/000724 filed 28 Jan. 2004 which designated the U.S. and claims benefit of IT MO2003A000019, dated 28 Jan. 2003, the entire contents of each of which are hereby incorporated by reference.

The invention relates to an apparatus and a method of electro-stimulation and a data support that can be read by a processing device. On the data support data are recorded that are required for the operation of the apparatus and the actuation of the method.

The apparatus and the method of electro-stimulation according to the invention are particularly suitable for carrying out bioactive neuro-stimulation and for modulation of cytokines, growth factors and of enzymatic cellular metabolism.

Clinical data show that more than half of the population of western countries suffers from vascular pathologies, and in particular pathologies affecting the cardiovascular system. Alterations of the vascular walls frequently occur that are caused by degenerative pathologies such as arteriosclerosis which, together with thrombosis, is one of the most frequent causes of obstruction of the peripheral arteries and of those that affect the myocardium and the brain.

Arteriosclerosis manifests itself in a particularly aggressive and premature manner in diabetic patients, who make up about 3% of the European population and a similar percentage of the population in Italy. This pathology is accompanied by long-term complications that gravely disable the patient that are due to the degeneration of the larger blood vessels (macro-angiopathy), of the smaller blood vessels (micro-angiopathy) and of the peripheral and vegetative nervous system (neuropathy). Peripheral macro-angiopathy in diabetic patients produces analogous symptoms to those observed in non-diabetic patients; however, this manifests itself prematurely, with greater frequency and deteriorates rather rapidly.

For the above explained reasons, the vascular pathologies causes in diabetic patients a mortality rate twice the mortality rate in non-diabetic patients, and make long hospitalisations necessary, with remarkable economic and social consequences.

Furthermore, in diabetic patients arteriosclerosis is responsible for a majority of the amputations of the lower limbs (50-70%), which such patients undergo 5 times more frequently than non-diabetic patients. The occlusion of small and medium-calibre distal arteries below the knee causes gangrene to develop. Furthermore, diabetic patients suffer more frequently than non-diabetic patients from claudicatio intermittens due to ischemia of the muscles in the calves, the thigh or the gluteus.

Substances have recently been discovered and described in the literature that are produced by endothelium cells and cause new blood vessels to be formed (angiogenesis) and vasodilatation, such as, for example, the Fibroblast Growth Factor (FGF), Neuronal Growth Factor (NGF), Epithelial Growth Factor (EGF), Vascular Endothelial Growth Factor (VEGF) and Angiopoietin-2.

To promote angiogenesis, VEGF and other angiogenic factors, such as FGF, can be injected directly into the vascular bed affected by ischemia and/or occlusion.

But the direct injection of VEGF or other angiogenic factors has many drawbacks, which are mainly due to the difficulty of release to all the cells affected. In fact, less than 2% of the VEGF injected is effectively involved in neo-angiogenesis; furthermore, the method is potentially toxic.

Experiments conducted by Kanno et. al. have shown that when continuous electrical stimulation was applied for 5 days to isolated animal muscles by means of pulses having a width of 0.3 ms, a frequency of 50 Hz and an intensity of 0.1 V, an increase in the production of VEGF was observed and neo-angiogenesis was promoted through an increase in the number of capillaries and of the blood flow.

Although said experiments seem to suggest that electric stimulation of the muscles has beneficial effects on the circulation they do not teach how to apply electric stimulation to humans.

In addition, they require treatment lasting several days, which could cause the patient discomfort because of its excessive length.

Furthermore, it is known to use laser transmyocardial rivascularisation to reduce the pain caused by angina; this determines an increase in the level of VEGF in the myocardium and in the endothelium cells of capillaries and arterioles (Lee, S H, Wolf P L, Escudero R, N Eng. J. Med. 2000; 342, 626-33). However, laser transmyocardial rivascularisation is an invasive technique that achieves limited results.

US 2002/0010492 describes an electro-stimulation device for the controlled production of angiogenic growth factors, through which device the level of VEGF can be increased in vitro by 30-40% through continuous electro-stimulation lasting at least 8 hours.

However, even in this case, long periods of treatment are required that cause significant discomfort to the patient.

WO 02/09809 discloses an apparatus for treating vascular, muscular or tendinous pathologies by means of which a series of pulses having a width from 10 to 40 µs and an intensity from 100 to 170 µA is applied to the patient. In this way, an increase in the production of VEGF can be obtained, with consequent vasodilatation and neo-angiogenesis.

An object of the invention is to improve the condition of patients affected by vascular pathologies, and more in particular of diabetic patients suffering from said pathologies.

A further object of the invention is to stimulate the production of large quantities of substances that promote the formation of new blood vessels and the dilatation of existing ones, in particular VEGF, with relatively short treatment time, i.e. without subjecting the patient to exhausting treatment lasting several hours.

In particular, it is desired to induce production of VEGF or of other growth factors in quantities that are substantially greater than those obtained by means of the apparatus described in WO 02/09809.

In a first aspect of the invention, there is provided an electro-stimulation apparatus, comprising an electric-pulse generating device arranged to generate pulses having preset values of typical parameters, an applying arrangement arranged to apply a sequence of said pulses to an organism, said sequence comprising an initial pulse and a final pulse, wherein it further comprises a variation arrangement arranged to perform a substantial variation of at least one typical parameter at a moment comprised between said initial pulse and said final pulse.

In a second aspect of the invention, there is provided a method of electro-stimulating an organism, comprising generating a sequence of electric pulses having preset values of typical parameters, said sequence comprising an initial pulse and a final pulse, and applying said sequence to said organism, wherein said generating comprises considerably varying at least one typical parameter at a moment comprised between said initial pulse and said final pulse.

In a third aspect of the invention, there is provided a support readable by a data processing device, containing a plurality of data with preset values of typical parameters, said data being intended to originate a sequence of electric pulses to be applied to an organism by means of electro-stimulation techniques, said sequence comprising an initial pulse and a final pulse, wherein a substantial variation of at least one typical parameter is provided in said sequence at a moment comprised between said initial pulse and said final pulse.

In one embodiment, the parameter that is considerably varied is the frequency of the pulses.

In a further embodiment, the parameter that is considerably varied undergoes a decrease in its value.

This decrease can be of an order of magnitude.

As will described in detail below, experimental data have shown that owing to the invention and particularly owing to the substantial variation occurring in one of the typical parameters in the sequence of electric pulses, it is possible to obtain a relaxing effect on the muscle fibres, an activating effect on the vessels and on the neuroreceptors and a release of growth factors. It is furthermore possible to obtain an anti-inflammatory effect and to inhibit the cytokines that cause the inflammation. Finally, the invention enables stimulation of the small neurological afferent fibres and better interaction with the motor system to be obtained.

As the good effects that have been noted are linked to the substantial variation of a typical parameter that occurs in an almost instantaneous manner, it is no longer necessary to subject the patient to treatment lasting several hours, because a session of only a few minutes enables said improvements to be observed.

Furthermore, the electric pulses can be applied transcutaneously, i.e. by using a technique that is not invasive and does not cause to the patient particular discomfort.

In order that the invention may be clearly and completely disclosed, reference will now be made, by way of examples that do not limit the scope of the invention, to the accompanying drawings, in which.

An apparatus for electro-stimulation comprises one or more generators of electric pulses that can be controlled by a control device provided with a microprocessor. The control device can modulate the frequency and/or the width and/or the intensity of the electric pulses according to preset sequences. The electric pulses can be sub-threshold, i.e. maintained below values that could cause contraction of the muscle or a sensation of pain in the patient.

The apparatus further comprises an applying arrangement for applying the electric pulses to an organism, for example a human or a laboratory animal. The applying arrangement may comprise electrodes provided with a highly conductive surface that are positioned directly on the skin of the patient to transcutaneously transmit the pulses.

The parameters that distinguish the pulses are defined on the basis of the rheobasis and/or of the chronaxy of the stimulated neuro-muscular tissue, or in general on the basis of the bioreaction. Rheobasis is intended as the minimum current intensity required to excite a tissue, whereas chronaxy is the minimum duration that an electric pulse having twice the intensity of the rheobasis must have to generate a stimulation.

Bioreaction is defined as the time that elapses between a trailing edge of an applied pulse and the leading edge of the following pulse, i.e. the biological reaction time available to a preset tissue before the application of the following pulse.

A variation arrangement is furthermore provided arranged to vary the typical parameters of the applied pulses, namely the frequency and/or the width and/or the intensity.

In a first embodiment, the pulses generated by the apparatus according to the invention have a width from 1 to 90 µs and a frequency from 0.1 Hz to 1 kHz. Their peak voltage is above 50 V and may vary up to 300 V.

In a second embodiment, the pulses have a width between 1 and 49 µs, a frequency from 0.1 Hz to 100 Hz and a peak voltage up to 200 V.

In a third embodiment, the width of the pulses varies from 1 to 40 µs, the frequency varies from 0.1 Hz to 100 Hz and peak voltage reaches a maximum of 300 V.

The electro-stimulation apparatus is configured in such a way as to apply a sequence of stimuli comprising a preset succession of sub-sequences. Each sub-sequence is the result of the modulation of frequency, width and intensity according to a protocol that depends on the biochemical effect that is desired to have on the cells and on the tissues.

For example, to obtain a relaxing effect on the muscular fibres, a sequence of sub-threshold pulses is applied which stimulates the muscle with a gradually increasing frequency, until a condition of tetany is reached in which the muscle reaches a spasm situation. Frequency is thereafter sharply reduced to the value of 1 Hz, so as to create a traumatic event and cause muscular relaxation.

Figure 1:
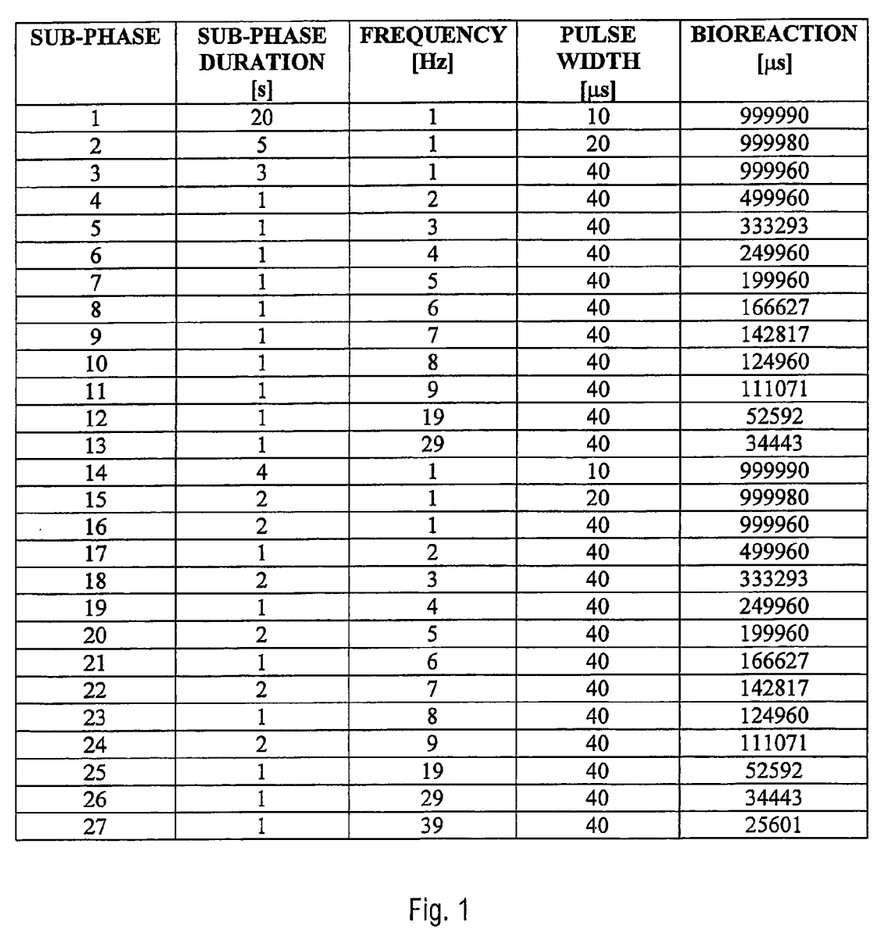
FIG. 1 is a table disclosing the sub-phases of a stimulation sequence with relaxing effect.

One example of said sequence is shown in FIG. 1, and comprises 27 sub-phases according to the indicated parameters. In the first sub-phase, pulse trains are sent to the patient for a time interval having a duration of 20 seconds. In this period, the frequency has a value of one pulse per second (1 Hz), each pulse having a width of 10 microseconds. During the second sub-phase, which lasts 5 seconds, the pulse trains applied to the patient have a pulse frequency of 1 Hz, and each pulse has a duration of 20 microseconds. The frequency of the pulses of each sub-phase is then gradually increased until the sub-phase 13 is reached, in which the frequency reaches a value of 29 Hz with a pulse width of 40 microseconds. In the following sub-phase there is a sudden decrease in the frequency of the pulses, which drops by an order of magnitude from 29 Hz to 1 Hz, and in the pulse width, which decreases from 40 microseconds to 10 microseconds. After this sudden decrease, the frequency and the pulse width are increased again in a gradual manner, until they reach a final value of respectively 39 Hz and 40 microseconds.

Experimental results have shown that the sudden decrease in the pulse frequency applied to the muscle allows the muscle to relax. To reinforce the positive effects of the decrease in frequency, it is possible to repeat the sequence in FIG. 1 several times, in which case the frequency discontinuity occurs a greater number of times.

On the other hand, in order to obtain an effective action on the blood vessels and an anti-inflammatory effect, substances have to be released such as the growth factors promoting neoangiogenesis and producing cytokines, that are able to produce an anti-inflammatory effect. At the same time, the formation of other cytokines such as TNF-α, interleukin-6, interferone-α and cortisole, that are responsible for the inflammatory state, has to be inhibited.

In order to do this without stimulating the tissue for an excessively long time and with a marginal release of energy, sequences of pulses are applied to the patient in which the frequency is rapidly increased until the required value is reached. This value varies according to the substance to be released, produced or inhibited.

The inventor thinks that the electrical field applied by the electro-stimulation apparatus creates a series of vibrations by pulse polarisation and depolarisation of the cells and of the molecules. Such vibrations induce resonance conditions in sub-structures of the cells of the connective tissue, and in particular in the sub-structures of the endothelium cells, of the muscles, of the dermis and of the epidermis, for example the cell membrane, mitochondria, and/or the immunological molecules or complexes. This causes specific enzymes, cytokines and growth factors to be released into the interstitial spaces and therefore into the circulating blood.

Depending on the different model of resonance induced in the cellular sub-structures, a release or transcription of different molecules is obtained. Therefore, by appropriately varying the frequency of the pulses applied, it is possible to reach the typical resonance frequency corresponding to the type of molecule that one wishes to release or inhibit.

Figure 2:
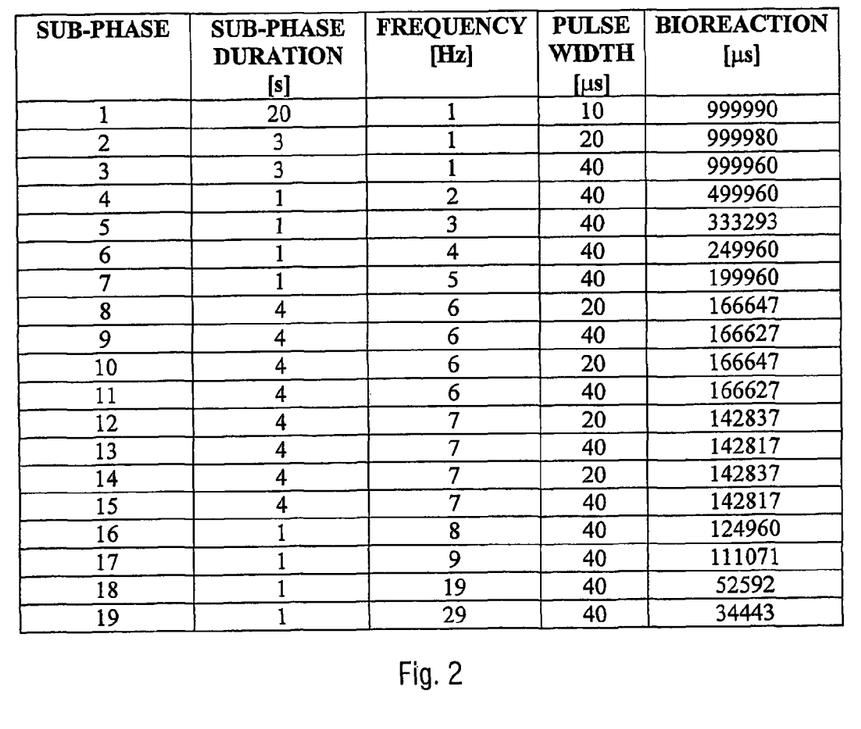
FIG. 2 is a table disclosing the sub-phases of a stimulation sequence with anti-inflammatory effect.

One example of a sequence of pulses to apply in order to obtain an anti-inflammatory effect, operating according to the mechanism above-described, is set out in FIG. 2.

Figure 3:
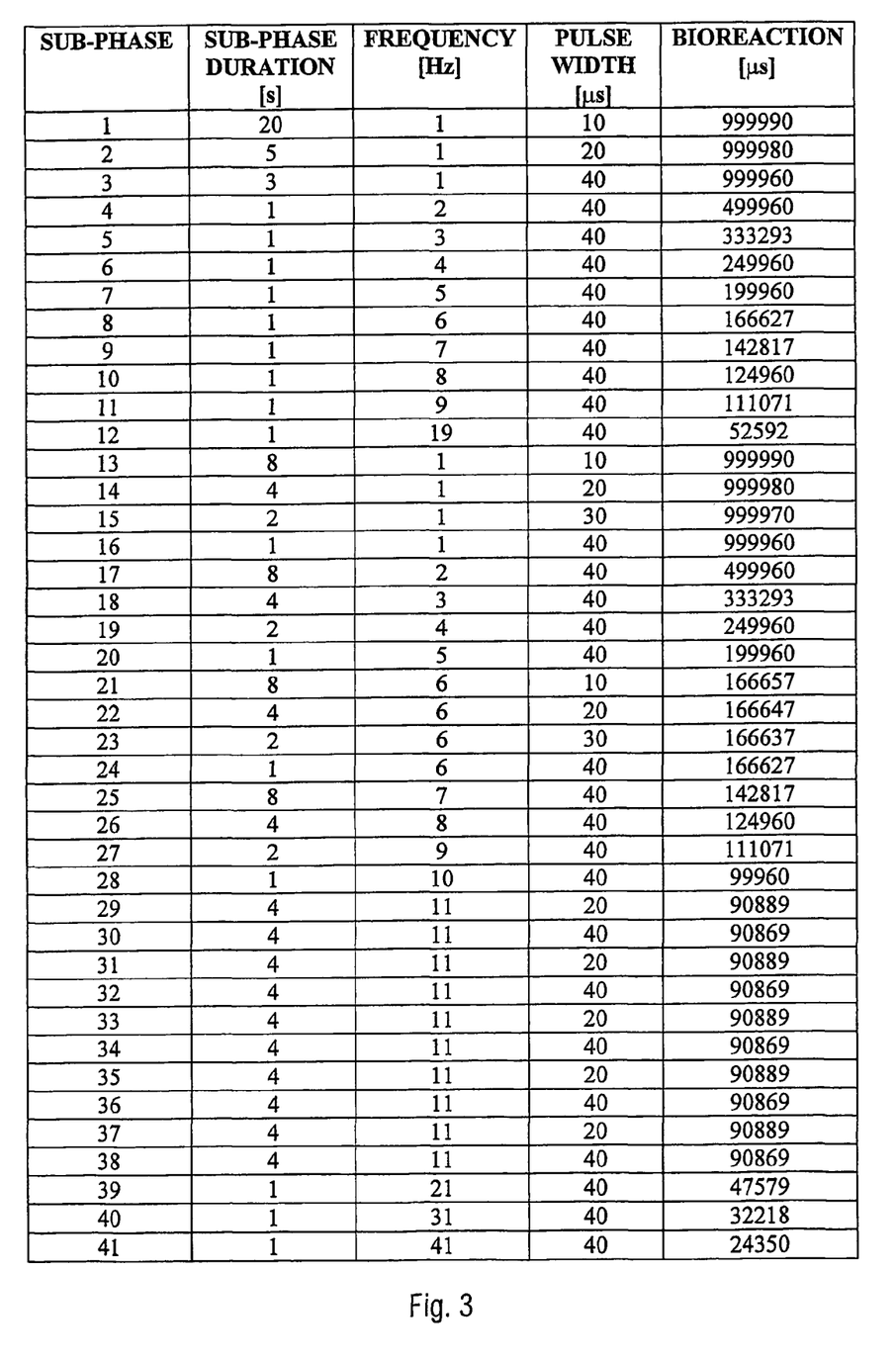
FIG. 3 is a table disclosing the sub-phases of a stimulation sequence for activating the microcirculatory system.
Figure 4:
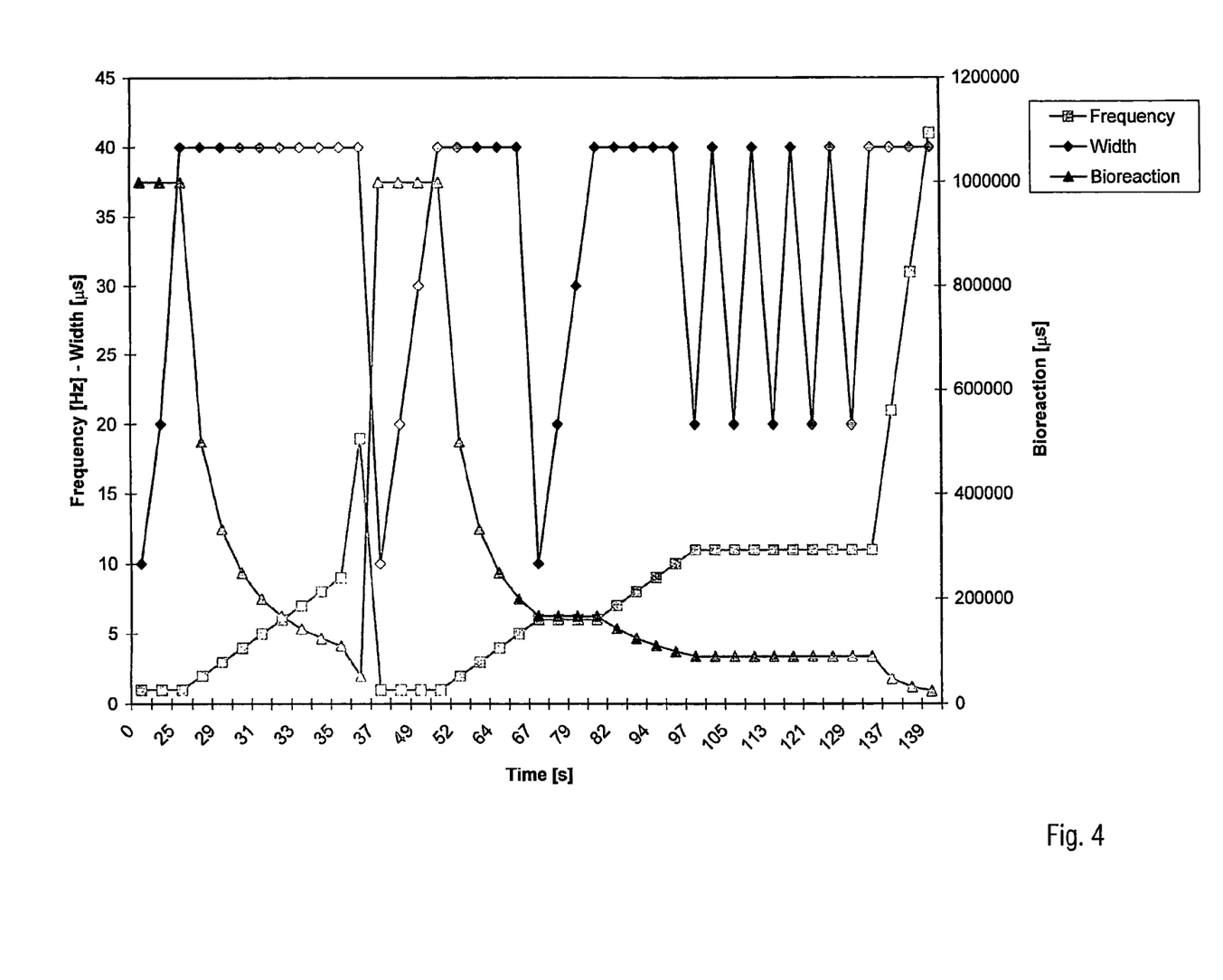
FIG. 4 shows the variation of the operational parameters during the sequence for activating the microcirculatory system shown in FIG. 3.

If it is rather desired to activate the microcirculatory system, a sequence of the type shown in FIG. 3 can be applied. The variations of the typical parameters of the pulse for this latter sequence are shown in FIG. 4.

As can be noted, the sequence shown in FIG. 3 comprises an initial sub-sequence that is substantially analogous to the initial part of the sequence shown in FIG. 1 and that aims to obtain a relaxing effect. Subsequently, during sub-phase 13 the frequency is sharply reduced to the value of 1 Hz and subsequently increased up to 11 Hz. After this, the frequency is kept constant for a few seconds in order to cause an effective vaso-action on the blood vessels. Then, from sub-phase 38, the value of the frequency is increased by 10 Hz at each sub-phase, until the value of 41 Hz is reached, around which value it has been experimentally established that the greatest release of VEGF is obtained. Said frequency reasonably seems to be the resonance frequency of VEGF.

In order to obtain an even higher level of VEGF in the blood, the sequence shown in FIG. 3 can be repeated several times a day.

By repeating the same sequence several times in succession, a surprising synergic effect was observed, inasmuch as it was seen that the obtained result was greater than the sum of the results that could logically be expected by applying two sequences independently of each other.

This seems to be due to the sudden reduction in the frequency of the pulses applied, i.e. the sharp transition from a relatively high frequency value to the initial value of 1 Hz, which introduces a discontinuity in the applied pulses. This results in a significant energy variation. By repeating the sub-sequence several times, an effect analogous to the so-called "water hammer" occurring in hydraulics takes place, by means of which the stimulation by sub-threshold electric pulses enables weak chemical bonds to be broken and large quantities of the desired molecules to be released or transformed, without inducing a significant transfer of energy to the tissue.

In one embodiment, the variation in the applied frequency is greater than 20 Hz. In another embodiment, the variation in the applied frequency is greater than 40 Hz. In a further embodiment, such variation may be greater than 60 Hz.

The above-formulated hypothesis was experimentally tested by stimulating a lower limb of 10 diabetic patients, of 10 non-diabetic patients and of 10 healthy subjects whose behaviour was observed for control purposes. The pulses were applied to the peripheral distal part of the leg.

The stimulation sequence applied to all the individuals taking part in the experiment comprised two consecutive sub-sequences aimed to obtaining muscular relaxation, followed by two sub-sequences of activation of the microcirculatory system, in the manner described above. Stimulation was thereafter applied for a period of 10 minutes at a constant frequency of 100 Hz and with a constant pulse width of 40 microseconds.

Figure 6:
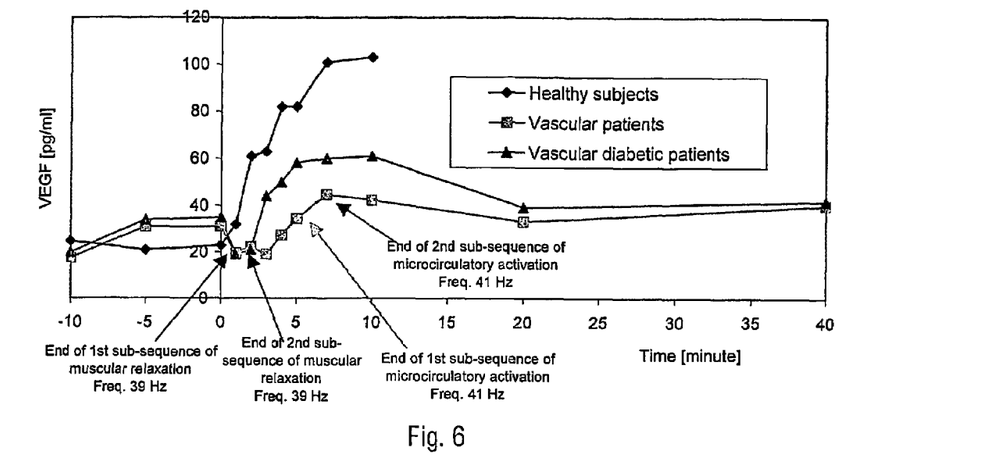
FIG. 6 shows the values of VEGF detected during experimental stimulation of a distal zone of the leg.
Figure 7:
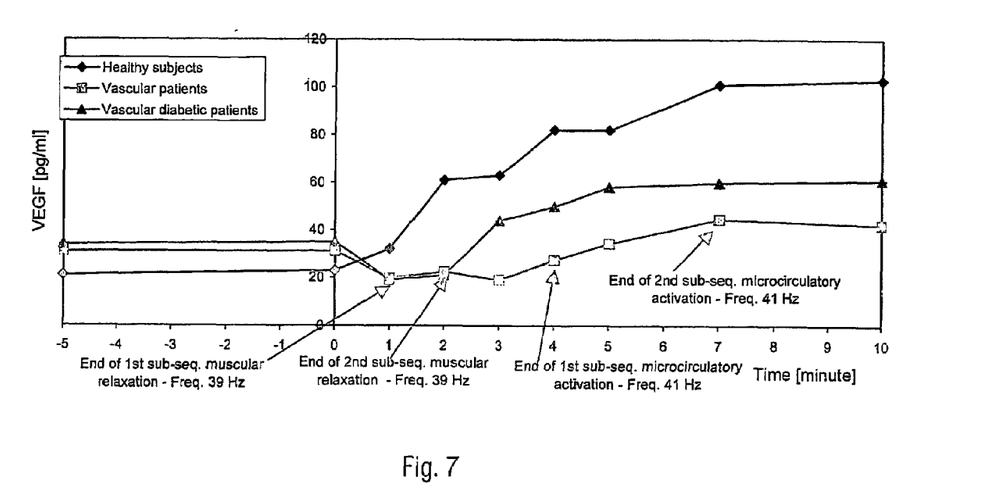
FIG. 7 shows a detail of FIG. 6.

Blood samples from the systemic circulation were taken of the individuals taking part in the experiment (samples were taken from the brachial vein) 10 and 5 minutes before stimulation, and 0, 1, 2, 3, 4, 5, 7, 10, 20 and 40 minutes after the beginning of stimulation. The results obtained are shown in FIGS. 5, 6 and 7.

Figure 5:
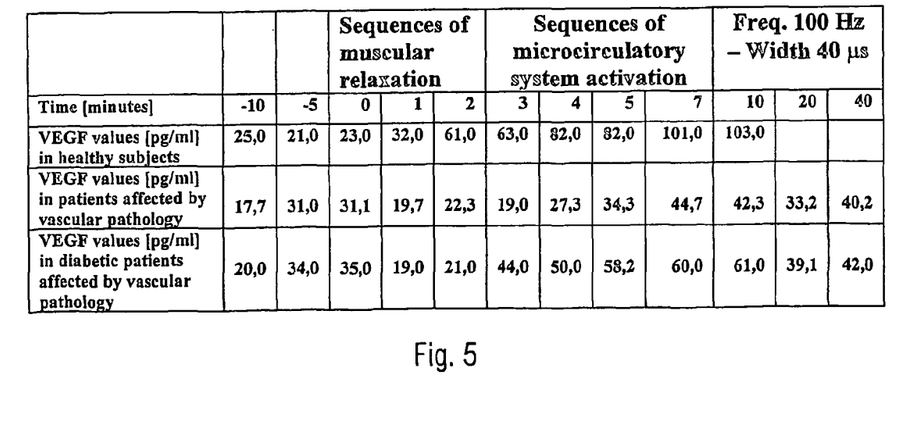
FIG. 5 is a table disclosing the levels of VEGF found in patients subjected to electro-stimulation treatment according to the invention.

In particular, FIG. 5 shows the average VEGF values measured in the blood samples taken from the different patients at the times indicated. The values at −10 and −5 minutes refer to the period preceding stimulation, the values at 0, 1 and 2 minutes were recorded during the sub-sequences of muscular relaxation, the values at 3, 4, 5 and 7 minutes were recorded during the sub-sequences of activation of the microcirculatory system. The values at 10, 20 and 40 minutes were recorded during the final sub-sequence at a constant frequency and width. The recorded VEGF pattern is set out graphically in FIGS. 6 and 7.

As can be noted, at the end of every sub-sequence a sudden increase in the measured VEGF values occurred. The healthy subjects showed increases in VEGF that were up to 5 times greater than their base value, whereas in diabetic patients the VEGF value increased by up to 3 times more than the initial value.

It was furthermore noted that if electro-stimulation was not applied in an appropriate manner, VEGF did not increase. This was shown in the last phase, in which the frequency and the width of the pulses were kept constant and in both diabetic patients and in non-diabetic patients VEGF tended to decrease returning to the base values within 10 minutes.

Only when the stimulation frequency was appropriately modified in such a manner as to reach the typical resonance frequency of the cells that produce VEGF, and then suddenly decreased to create a traumatic event, an effective and consistent increase in the growth factor occurred, through a mechanism that in certain respects is analogous to the one that determines the so-called "water hammer".

The detected increases in VEGF, as shown in FIGS. 5, 6 and 7, appear to be particularly significant if one considers that they were measured in the blood samples taken from the brachial veins of the subjects examined, whereas electro-stimulation was carried out in the distal peripheral part of the leg. This means that the VEGF that had been produced in the stimulated zone, rapidly spread throughout the organism, thereby determining a considerable increase in the average value of VEGF current in the patient's blood at the systemic level.

Therefore the increase in VEGF from the value of 21 pg/ml recorded after 2 minutes of electro-stimulation, to the value of 60 pg/ml measured after 7 minutes of electro-stimulation in the blood taken from the brachial veins of the diabetic patients is indicative of a much more considerable increase in VEGF in the stimulated zone that is affected by the occlusion of the blood vessels. This results, in the stimulated zone, in a substantial benefit to the patient deriving from the formation of new blood vessels and from the dilatation of existing ones.

Figure 8:
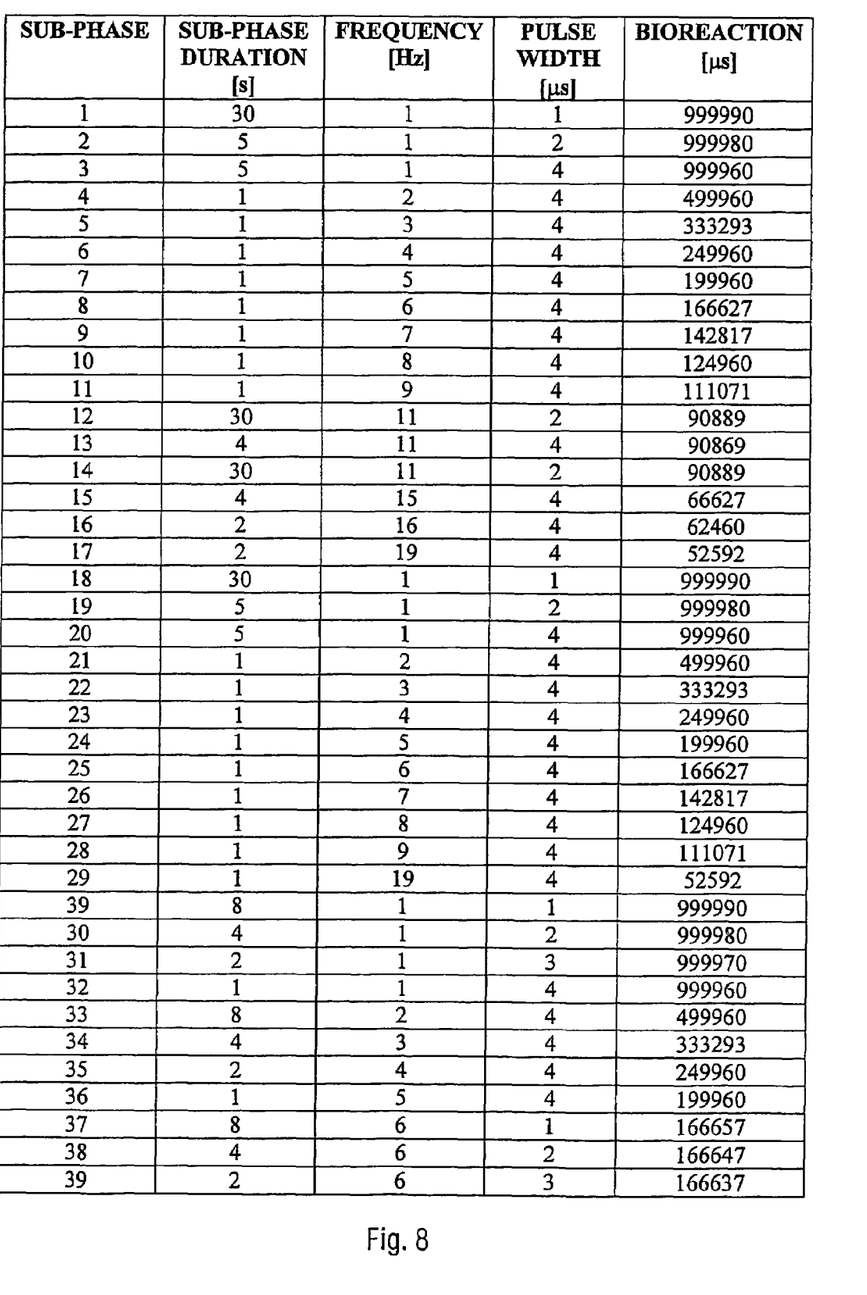
FIG. 8 shows the sub-phases of the first part of a neuro-muscular stimulation sequence of the hypotonic muscle.
Figure 9:
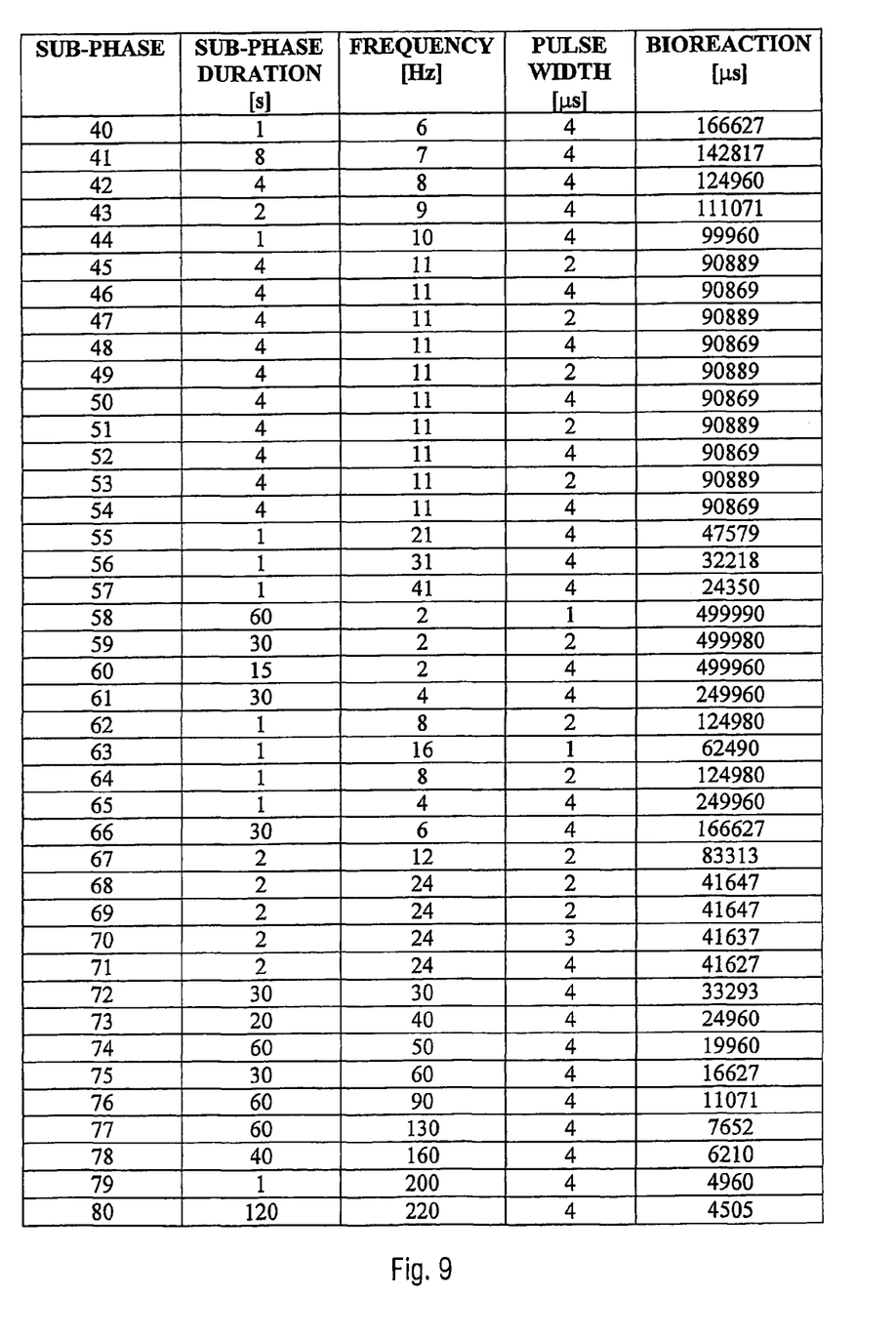
FIG. 9 shows the sub-phases of the second part of a sequence, the first part of which is shown in FIG. 8.

Lastly, it has been proposed to use a sequence like the one shown in FIGS. 8 and 9 to stimulate small afferent neurological fibres and their interaction with the motor units. The data shown in FIGS. 8 and 9 actually constitute a single sequence, which has been set out on two separate sheets for the sake of clarity.

As can be noted, this last sequence is a combination of a modified sub-sequence of muscular relaxation, followed by a vasoactive sub-sequence. A sub-sequence activating the small nervous fibres is then provided until a pulse frequency of 220 Hz is reached. This produces a gradual increase in prioreception and in peripheral sensitivity in patients affected by paraplegia, tetraplegia or hemiplegia, secondary lesions to the brain, traumas to the head or to the spine, or apoplectic stroke.

According to an embodiment of the invention, the pulse width can also be varied and in particular it can be increased from the current value until a preset maximum value is reached. This maximum value can be of about 90-100 μs.

The increase in pulse width is equal to a percentage of the current pulse width value, for example 20%, 25%, 33% or 50% of the current value. Experimental tests have shown that the best results are obtained if percentage increases of 20% of the current pulse width value are chosen.

Between an increase in pulse width and the subsequent increase, a time interval occurs having a duration which can be randomly varied between a minimum value and a maximum value. In particular, the minimum value of this duration can be of about 15 seconds, whereas the maximum value can be of about 60 seconds.

When the preset maximum pulse width is reached, the pulse width is suddenly decreased to its initial value.

This variation of the pulse width can be repeated several times. It can in particular be applied when the pulse frequency is kept constant, for example when, after applying to the patient the sequences previously disclosed with reference to the drawings, stimulation is applied for some minutes at a constant frequency.

By varying the pulse width, adaptation phenomena are avoided in the patient, which means that the patient does not get used to the applied pulses, which might decrease the therapy efficiency.

The invention claimed is:

1. Electro-stimulation apparatus, comprising an electric-pulse generating device arranged to generate pulses having preset values of typical parameters, an applying arrangement arranged to apply a number of sub-phases forming a sequence of said pulses to an organism, said sequence comprising an initial pulse and a final pulse, said apparatus further comprising a variation arrangement arranged to perform a substantial variation of at least one typical parameter at a moment comprised between said initial pulse and said final pulse, said variation arrangement comprising means programmed to vary frequency of said pulses by causing between two consecutive sub-phases a frequency discontinuity greater than 60 Hz preceded by sub-phases having non-constant frequencies.

2. Apparatus according to claim 1, wherein said variation arrangement comprises means for causing a sudden decrease in the value of said at least one typical parameter.

3. Apparatus according to claim 2, wherein said generating device comprises means for causing a gradual increase in the value of said at least one typical parameter, before said sudden decrease.

4. Apparatus according to claim 3, wherein during said gradual increase progressive increments of said at least one typical parameter are provided, said progressive increments being smaller than said sudden decrease by an order of magnitude.

5. Apparatus according to claim 2, wherein said generating device comprises means for causing a further gradual increase in the value of said at least one typical parameter, after said sudden decrease.

6. Apparatus according to claim 1, wherein said variation arrangement is so configured as to actuate said substantial variation when a spasm condition of a muscle stimulated in said organism is reached.

7. Apparatus according to claim 1, wherein said variation arrangement is so configured as to actuate said substantial variation when a frequency is reached at which a major release of growth factors, particularly of VEGF, occurs.

8. Apparatus according to claim 1, wherein said generating device is so arranged as to generate within said sequence first pulses having a gradually increasing frequency according to a first increment, and second pulses having a gradually increasing frequency according to a second increment, said second increment being greater than said first increment.

9. Apparatus according to claim 8, wherein said second increment is greater by an order of magnitude than said first increment.

10. Apparatus according to claim 8, wherein said sequence comprises, between said first pulses and said second pulses, an intermediate series of pulses with a substantially constant frequency.

11. Apparatus according to claim 10, wherein said intermediate series comprises pulses having a pulse width oscillating between a maximum and a minimum value, said maximum value being substantially equal to twice said minimum value.

12. Apparatus according to claim 1, wherein after said variation said at least one typical parameter remains constant for a number of sub-phases.

13. Apparatus according to claim 1, wherein said generating device is arranged to generate a further sequence of electrical pulses after said sequence, so that said variation is repeated more than once.

14. Apparatus according to claim 1, wherein said variation arrangement comprises means arranged to vary the width of said pulses.

15. Apparatus according to claim 14, wherein said variation arrangement is so configured as to increase the width of said pulses by applying percentage increments of the current width value.

16. Apparatus according to claim 15, wherein said percentage increments are selected from a group consisting of: 20% of the current width value, 25% of the current width value, 33% of the current width value, 50% of the current width value.

17. Apparatus according to claim 15, wherein between a percentage increment and the subsequent percentage increment a time interval occurs which is randomly selected.

18. Apparatus according to claim 17, wherein said time interval can be varied between 15 s and 60 s.

19. Apparatus according to claim 18, wherein the width of said pulses is increased up to a maximum value of about 90-100 µs.

20. A method of electro-stimulating an organism, comprising generating electric pulses having preset values of typical parameters and applying a number of sub-phases forming a sequence of said pulses to said organism, said sequence comprising an initial pulse and a final pulse, wherein said generating comprises the step of varying considerably at least one typical parameter at a moment comprised between said initial pulse and said final pulse and wherein the step of varying comprises modifying frequency of said pulses by causing between two consecutive sub-phases a frequency discontinuity greater than 60 Hz preceded by sub-phases having non-constant frequencies.

21. A method according to claim 20, wherein said varying comprises suddenly decreasing the value of said at least one typical parameter.

22. A method according to claim 21, wherein said generating comprises gradually increasing the value of said at least one typical parameter, before said suddenly decreasing.

23. A method according to claim 22, wherein during said gradually increasing progressive increments of said at least one typical parameter are applied, said progressive increments being smaller than the decrease applied during said suddenly decreasing by an order of magnitude.

24. A method according to claim 21, wherein said generating comprises further gradually increasing the value of said at least one typical parameter, after said suddenly decreasing.

25. A method according to claim 20, wherein said varying occurs when a spasm condition of a muscle stimulated is reached in said organism.

26. A method according to claim 20, wherein said varying takes place when a frequency is reached at which a major release of growth factors, particularly of VEGF, occurs.

27. A method according to claim 20, wherein said generating comprises providing within said sequence first pulses having a gradually increasing frequency according to a first increment, and second pulses having a gradually increasing frequency according to a second increment, said second increment being greater than said first increment.

28. A method according to claim 27, wherein said second increment is greater by an order of magnitude than said first increment.

29. A method according to claim 27, wherein said sequence comprises, between said first pulses and said second pulses, an intermediate series of pulses with a substantially constant frequency.

30. A method according to claim 29, wherein said intermediate series comprises pulses having a width oscillating between a maximum and a minimum value, said maximum value being substantially equal to twice said minimum value.

31. A method according to claim 20, wherein after said varying, said at least one typical parameter is kept constant for a number of sub-phases.

32. A method according to claim 20, wherein said generating comprises further generating a further sequence of electrical pulses, so that said varying is repeated more than once.

33. A method according to claim 20, wherein said varying comprises modifying the width of said pulses.

34. A method according to claim 33, wherein said modifying comprises increasing the width of said pulses by applying percentage increments of the current width value.

35. A method according to claim 34, wherein said percentage increments are selected from a group consisting of: 20% of the current width value, 25% of the current width value, 33% of the current width value, 50% of the current width value.

36. A method according to claim 35, wherein between a percentage increment and the subsequent percentage increment a time interval occurs which is randomly selected.

37. A method according to claim 36, wherein said time interval can be varied between 15 s and 60 s.

38. A method according to claim 33, wherein the width of said pulses is increased up to a maximum value of about 90-100 µs.

39. A support readable by a data processing device, containing a plurality of data with preset values of typical parameters, said data being intended to originate a number of sub-phases forming a sequence of electric pulses to be applied to an organism by means of electro-stimulation techniques, said sequence comprising an initial pulse and a final pulse, wherein a substantial variation of at least one typical parameter is provided in said sequence at a moment comprised between said initial pulse and said final pulse, said substantial variation comprising, between two consecutive sub-phases, a frequency discontinuity greater than 60 Hz preceded by sub-phases having non-constant frequencies.

40. A support according to claim 39, wherein said variation comprises a sudden decrease in the value of said at least one typical parameter.

41. A support according to claim 40, wherein said sequence comprises a gradual increase in the value of said at least one typical parameter, before said sudden decrease.

42. A support according to claim 41, wherein during said gradual increase progressive increments of said at least one typical parameter are provided, said progressive increments being smaller than said sudden decrease by an order of magnitude.

43. A support according to claim 40, wherein said sequence comprises a further gradual increase in the value of said at least one typical parameter, after said sudden decrease.

44. A support according to claim 39, wherein said variation is provided when said at least one typical parameter reaches a value that causes a condition of spasm of a stimulated muscle in said organism.

45. A support according to claim 39, wherein said variation is provided when said at least one typical parameter reaches a value at which a major release of growth factors, particularly of VEGF, occurs.

46. A support according to claim 39, wherein said sequence comprises first pulses with a gradually increasing frequency according to a first increment, and second pulses with a gradually increasing frequency according to a second increment, said second increment being greater than said first increment.

47. A support according to claim 46, wherein said second increment is greater by an order of magnitude than said first increment.

48. A support according to claim 46, wherein said sequence comprises, between said first pulses and said second pulses, an intermediate series of pulses with a substantially constant frequency.

49. A support according to claim 48, wherein said intermediate series comprises pulses having a pulse width oscillating between a maximum and a minimum value, said maximum value being substantially equal to twice said minimum value.

50. A support according to claim 39, wherein after said variation said at least one typical parameter remains constant for a number of sub-phases.

51. A support according to claim 39, containing data that enable a further sequence of electrical pulses to be generated after said sequence, so that said variation is repeated more than once.

52. A support according to claim 39, wherein said variation comprises a sudden change in the width of said pulses.

53. A support according to claim 52, wherein said width is increased by applying percentage increments of the current width value.

54. A support according to claim 53, wherein said percentage increments are selected from a group consisting of: 20% of the current width value, 25% of the current width value, 33% of the current width value, 50% of the current width value.

55. A support according to claim 50, wherein between a percentage increment and the subsequent percentage increment a time interval occurs which is randomly selected.

56. A support according to claim 55, wherein said time interval can be varied between 15 s and 60 s.

57. A support according to claim 52, wherein the width of said pulses is increased up to a maximum value of about 90-100 s.

* * * * *